(12) United States Patent
Hvid et al.

(10) Patent No.: US 10,434,241 B2
(45) Date of Patent: Oct. 8, 2019

(54) SYSTEM FOR ANAL OR STOMAL IRRIGATION, AND A METHOD FOR PREDICTING A TEMPERATURE OF AN IRRIGATION LIQUID IN A RESERVOIR OF SUCH SYSTEM

(71) Applicant: Coloplast A/S, Humlebaek (DK)

(72) Inventors: Niels Hvid, Vedbaek (DK); Richard Morgan Hickmott, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 176 days.

(21) Appl. No.: 15/536,672

(22) PCT Filed: Dec. 17, 2015

(86) PCT No.: PCT/DK2015/050404
§ 371 (c)(1),
(2) Date: Jun. 16, 2017

(87) PCT Pub. No.: WO2016/095930
PCT Pub. Date: Jun. 23, 2016

(65) Prior Publication Data
US 2017/0340804 A1    Nov. 30, 2017

(30) Foreign Application Priority Data
Dec. 19, 2014  (DK) .................. 2014 70808

(51) Int. Cl.
*A61M 3/02* (2006.01)
*A61F 5/442* (2006.01)
(Continued)

(52) U.S. Cl.
CPC .......... *A61M 3/0254* (2013.01); *A61F 5/442* (2013.01); *A61M 3/0245* (2013.01);
(Continued)

(58) Field of Classification Search
CPC ............ A61M 3/0254; A61M 2205/18; A61M 2205/3368; A61M 2210/1067;
(Continued)

(56) References Cited

U.S. PATENT DOCUMENTS 3,678,922 A  *  7/1972  Philips ................. A61B 5/0275
                                                      600/505
4,574,359 A     3/1986  Ishizaka et al.
(Continued)

FOREIGN PATENT DOCUMENTS

| CN | 201469754 U | 5/2010 |
|---|---|---|
| CN | 201710720 U | 1/2011 |

(Continued)

*Primary Examiner* — Lisa M Caputo
*Assistant Examiner* — Philip L Cotey
(74) *Attorney, Agent, or Firm* — Coloplast Corp., Coloplast A/S; Nick Baumann (57) ABSTRACT

A system for anal or stomal irrigation comprises a reservoir (102) for an irrigating liquid; a catheter (100) comprising a catheter tip for insertion into the rectum or stoma, a thermo sensor (128) connected to the reservoir for obtaining a measure of a temperature within the reservoir, a tubing system and/or the catheter. A control system (103) operatively connected with the thermo sensor is configured to determine a temperature within the reservoir. A method for predicting a temperature in a reservoir for irrigation liquid is also provided.

13 Claims, 9 Drawing Sheets

(51) Int. Cl.
*A61M 25/00* (2006.01)
*G01K 3/10* (2006.01)
*G01K 13/02* (2006.01)

(52) U.S. Cl.
CPC ...... *A61M 3/0258* (2013.01); *A61M 25/0067* (2013.01); *G01K 3/10* (2013.01); *G01K 13/02* (2013.01); *A61M 2205/18* (2013.01); *A61M 2205/3368* (2013.01); *A61M 2205/502* (2013.01); *A61M 2210/1067* (2013.01)

(58) Field of Classification Search
CPC ............ A61M 3/0258; A61M 25/0067; A61M 2205/502; A61F 5/442; G01K 3/10; G01K 13/02
See application file for complete search history.

(56) References Cited

U.S. PATENT DOCUMENTS

| | | | |
|---|---|---|---|
| 4,592,000 A | 5/1986 | Ishizaka et al. | |
| 4,638,436 A * | 1/1987 | Badger | A61N 7/02 600/549 |
| 4,648,055 A | 3/1987 | Ishizaka et al. | |
| 4,727,500 A | 2/1988 | Jackson et al. | |
| 4,843,577 A | 6/1989 | Muramoto | |
| 4,858,618 A * | 8/1989 | Konno | A61B 5/028 600/526 |
| 5,011,294 A | 4/1991 | Yamaguchi | |
| 5,066,141 A | 11/1991 | Ikeda et al. | |
| 5,080,496 A | 1/1992 | Keim et al. | |
| 5,190,519 A | 3/1993 | Mead et al. | |
| 5,473,629 A | 12/1995 | Muramoto | |
| 5,733,263 A | 3/1998 | Wheatman | |
| 5,738,441 A | 4/1998 | Cambridge et al. | |
| 6,139,571 A * | 10/2000 | Fuller | A61F 7/12 604/113 |
| 6,193,344 B1 | 2/2001 | Otsuka et al. | |
| 6,270,252 B1 * | 8/2001 | Siefert | G01K 7/42 374/102 |
| 6,789,937 B2 | 9/2004 | Haddad et al. | |
| 7,270,476 B2 | 9/2007 | Tokita et al. | |
| 7,809,254 B2 | 10/2010 | Lindsay et al. | |
| 7,988,353 B2 | 8/2011 | Yamamoto et al. | |
| 8,047,712 B1 * | 11/2011 | Sturner | G01K 7/425 374/1 |
| 8,061,149 B1 | 11/2011 | Gowans et al. | |
| 8,078,333 B2 | 12/2011 | Kienman et al. | |
| 8,197,128 B2 | 6/2012 | Zhang et al. | |
| 8,808,343 B2 | 8/2014 | Koch et al. | |
| 8,858,488 B2 | 10/2014 | Kelly et al. | |
| 8,868,357 B2 | 10/2014 | Huitt et al. | |
| 2004/0267339 A1 * | 12/2004 | Yon | A61F 7/12 607/105 |
| 2006/0122673 A1 * | 6/2006 | Callister | A61F 7/12 607/105 |
| 2006/0224349 A1 * | 10/2006 | Butterfield | G01K 7/42 702/130 |
| 2007/0116089 A1 | 5/2007 | Bisch et al. | |
| 2008/0114555 A1 * | 5/2008 | Scott | G01K 7/42 702/66 |
| 2008/0187022 A1 * | 8/2008 | Bellifemine | G01J 5/02 374/133 |
| 2008/0228246 A1 * | 9/2008 | Yon | A61F 7/12 607/106 |
| 2009/0270955 A1 * | 10/2009 | Magers | A61B 5/01 607/105 |
| 2009/0293734 A1 | 12/2009 | Quah | |
| 2010/0016787 A1 * | 1/2010 | Shapiro | A61M 3/0262 604/31 |
| 2010/0324635 A1 * | 12/2010 | Kreck | A61F 7/12 607/105 |
| 2012/0095537 A1 * | 4/2012 | Hall | A61M 1/285 607/105 |
| 2013/0310799 A1 | 11/2013 | Kammer et al. | |
| 2014/0199057 A1 | 7/2014 | Hansen et al. | |
| 2017/0319770 A1 * | 11/2017 | Fitzgerald | A61M 1/281 |

FOREIGN PATENT DOCUMENTS

| | | |
|---|---|---|
| CN | 202666070 U | 1/2013 |
| DE | 202012005708 U1 | 11/2013 |
| EP | 1206230 A1 | 5/2002 |
| EP | 2671602 A1 | 12/2013 |
| EP | 2679259 A1 | 1/2014 |
| WO | 0108614 A1 | 2/2001 |
| WO | 2006086826 A1 | 8/2006 |
| WO | 2009152568 A1 | 12/2009 |
| WO | 2011023196 A1 | 3/2011 |
| WO | 2012120456 A2 | 9/2012 |
| WO | 14018798 A2 | 1/2014 |

\* cited by examiner

SYSTEM FOR ANAL OR STOMAL IRRIGATION, AND A METHOD FOR PREDICTING A TEMPERATURE OF AN IRRIGATION LIQUID IN A RESERVOIR OF SUCH SYSTEM

The invention relates to a system and a method for anal and/or stomal irrigation comprising a reservoir for an irrigating liquid, and a catheter comprising a catheter tip for insertion into the rectum and/or stoma of a user. In particular, a control system is provided, the control system allowing a user to control or predict a future temperature of the irrigating liquid in the reservoir during filling or refilling thereof.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Control of voluntary bowel functions is frequently limited or absent in patients suffering from certain disabilities, such as spinal injuries, multiple sclerosis or bifid spine. Such lack of control of voluntary bowel functions typically results in faecal incontinence or intractable constipation, as patients have significantly reduced ability to sense the presence of faeces in the colon terminal part and the rectum and to sense the evacuation stimulus. Patients having undergone stomal surgery wherein a catheterizable stoma is constructed may suffer from similar difficulties.

It is known to accomplish bowel emptying by irrigation (i.e. flushing) of the rectum or stoma, by an irrigating fluid, such as tap water or saline, which is provided through an intermittent catheter with a tip which is configured and sized for insertion into the rectum or stoma, where it remains in a fixed position by an expandable inflation element, such as a balloon. The balloon may be inflatable by air or by water. Once the rectum or stoma has been flushed with the irrigating liquid, the expandable retention element is allowed to collapse to its non-deflated state, allowing the catheter to be withdrawn from the rectum or stoma, and allowing the liquid and faeces to evacuate. The catheter is connected to a reservoir of the irrigating liquid through a tube, and a pump may be provided for displacing the irrigating liquid from the reservoir to the catheter.

The development of transanal or transstomal irrigation systems has hitherto focussed on aspects of tubings, catheters and pumps. It is hence an object to improve known systems further, in particular by improving safety and user-convenience in relation to self-irrigation.

The user's bowels should be irrigated with liquid at a temperature not exceeding approximately 40° C., preferably at a temperature of 20-40° C., most preferably at a temperature of 36-38° C. Generally, systems for transanal or transstomal irrigation do not come with a heating or cooling element for the irrigating liquid, because such elements add to the costs of manufacturing and operating the system. Generally, the temperature of tap water used for anal or stomal irrigation of the user's bowel is controllable, albeit not in a precise manner. It is hence particularly an object to improve control of the temperature of the irrigating liquid in the reservoir in an easy-to implement and inexpensive manner.

Embodiments relate to a system for anal or stomal irrigation comprising:
  a reservoir for an irrigating liquid;
  a catheter comprising a catheter tip for insertion into the rectum or stoma of a user and for expelling of the irrigating liquid from the catheter tip;
  a tubing system providing a conduit for the irrigating liquid between the reservoir and the catheter tip;
  a pump operable to pump the irrigating liquid from the reservoir to the catheter tip;
  a thermo sensor connected to the reservoir for obtaining a measure of a temperature within the reservoir, the tubing system and/or the catheter;
  a control system operatively connected with the thermo sensor, the control system being configured to:
  determine a temperature within the reservoir.

Further embodiments relate to a method for predicting a temperature of an irrigating liquid in a reservoir of a system for anal or stomal irrigation, said system comprising further to said reservoir for the irrigating liquid:
  a catheter comprising a catheter tip for insertion into the rectum of a user and for expelling of the irrigating liquid from the catheter tip;
  a tubing system providing a conduit for the irrigating liquid between the reservoir and the catheter tip;
  a pump operable to pump the irrigating liquid from the reservoir to the catheter tip;
  a thermo sensor connected to the reservoir for obtaining a measure of a temperature within the reservoir, the tubing system and/or the catheter;
  a control system operatively connected with the thermo sensor;
  said method comprising operating the control system to:
  determine a temperature within the reservoir.

The temperature within the reservoir as determined by the thermo sensor may be a temperature of the irrigating liquid present in the reservoir, which may preferably be continuously measured, e.g. while the irrigating liquid is being filled into the reservoir. The temperature may be a current temperature or a predicted future temperature. The current or predicted temperature within the reservoir may conveniently be used to indicate to a user of the system if the current or predicted future temperature of the irrigating liquid is adequate. At the moment of use of the system for anal or stomal irrigation, the temperature of irrigating liquid within the reservoir should ideally be approximately 38° C., such as between 36° C. and 38° C., in order not to cause harmful effects to the user's tissue or to impart unpleasant sensations.

In one embodiment, the control system may be configured to indicate to the user if the current or predicted future temperature within the reservoir is outside a predetermined temperature range, such as below 36° C. or above 40° C. The control system may for example be configured to emit a warning signal if the current or predicted future temperature within the reservoir is below a predetermined lower limit or above a predetermined upper limit. The indication to the user, such as the warning signal, may be provided acoustically and/or optically via e.g. a graphical user interface of the system. The user may hence be allowed to ascertain if the temperature of the liquid supplied to the reservoir, typically tap water, is to be increased or decreased.

In a preferred embodiment of the invention, the control system is configured to
  determine the temperature within the reservoir before the irrigating liquid is filled or re-filled into the reservoir;
  determine an initial change of the temperature within the reservoir upon commencement of filling or refilling of the irrigating liquid into the reservoir;
  predict a future asymptotic value of the temperature within the reservoir on the basis of at least the initial change;
  continuously determine a current temperature or a current rate of change of the temperature within the reservoir while the irrigating liquid is filled or refilled into the reservoir; and
  continuously update the prediction of the future asymptotic value of the temperature within the reservoir on the basis of at least said current temperature and/or rate of change of the temperature.

A prediction of the future asymptotic value of the temperature within the reservoir once filled, notably of the irrigating liquid, may be made thanks to the provision of the thermo sensor. As the prediction of the future asymptotic temperature value is continuously updated on the basis of the current temperature and/or the rate of change of temperature, a change of temperature of the liquid supplied to the reservoir, such as for example a change of the ratio between hot and cold tap water, is adequately reflected in the temperature prediction. The temperature prediction may be communicated to the user, e.g. via a display of the system, thus assisting the user in ascertaining if the temperature of the supplied liquid, typically tap water, is to be increased or decreased.

Preferably, the thermo sensor is arranged to determine the temperature of the irrigating liquid itself, whereby the thermo sensor conveniently determines the temperature of the irrigating liquid itself. Alternatively, the thermo sensor may determine a temperature of a wall of the reservoir or of an element thermally coupled to the reservoir. The thermo sensor may conveniently be arranged within the reservoir at an inner wall thereof.

In order to improve precision of the prediction, the control system may configured to predict the future asymptotic temperature value on the basis of at least the initial change of temperature and further on the basis of at least one thermal characteristic of the system. For example, the thermo sensor may comprise a temperature sensitive element and a thermal conductor in contact with the temperature sensitive element, in which case the thermal characteristic of the system may comprise a thermal characteristic of the thermal conductor. The thermal conductor may for example comprise a rivet extending into the reservoir for the irrigating liquid, whereas the temperature sensitive element may be arranged outside the reservoir, such as at an outer wall thereof, embedded with a wall structure of the reservoir, or housed within a pump and control housing of the system. In order to obtain reliable temperature measurements at all times, the temperature sensitive element is preferably biased towards the thermal conductor.

In embodiments, in which the thermo sensor is mounted to a wall of the reservoir, the thermal characteristic of the system may comprise a thermal characteristic of the wall of the reservoir to take into account, e.g., its insulating properties and rectify the output of the temperature sensitive element in accordance therewith.

With a view to promoting heating of the irrigating liquid to the preferred temperature of approximately 36-38° C. under circumstances of lack of hot tap water, a heating element may be provided within the reservoir or attached thereto for forced heating of the irrigating liquid within the reservoir. The heating element may, for example, be controllable by the control system in response to the continuous temperature determination.

In embodiments, the catheter may comprise an expandable retention element for fixation of the catheter tip within the user's rectum or stoma. The conduit between the reservoir and the catheter tip may constitute a first conduit of the tubing system, and the tubing system may further comprise a second conduit between the reservoir and the expandable retention element. A valve system in the second conduit may be provided for controlling the flow of the irrigating liquid between the reservoir and the expandable retention element, and the pump and the valve system may be controllable to selectively:
  pump the irrigating liquid into the expandable retention element for expansion thereof;
  pump the irrigating liquid through the catheter for expelling of the irrigating fluid from the catheter tip and into the user's rectum or stoma;
  withdraw the irrigating liquid from the retention element for purging thereof.

The pump may be manually or electrically driven. The ability of the pump and the valve system to withdraw the irrigating liquid from the retention element for purging thereof allows the retention element to be purged in a controlled manner. Expansion of the retention element as well as collapsing thereof may hence be accurately controlled by adequate control of the pump and the valve system. Collapsing of the retention element by a controlled action, notably by forced purging caused by a pumping action of the pump enables purging of the retention element even under circumstances, at which the retention element is expanded by a relatively low pressure, which is too low for the irrigating liquid to escape from the retention element merely by opening a valve of the valve system.

The valve system within the tubing system is preferably configured to selectively cause one flow configuration selected from a first, second and third flow configuration at a time, wherein:
  the first flow configuration is arranged to cause a transfer the irrigating liquid, by means of said pump, from the reservoir into the expandable retention element;
  the second flow configuration is arranged to transfer the irrigating liquid, by means of said pump, from the reservoir to the catheter;
  the third flow configuration is arranged to transfer the irrigating liquid, by means of said pump, away from the expandable retention element.

Thus, in the first flow configuration the irrigating liquid is transferred from the reservoir to the expandable retention element for expansion thereof. In the second flow configuration, the irrigating liquid is transferred from the reservoir to the catheter, i.e. to the catheter tip for insertion into the user's rectum or stoma. In the third flow configuration, the irrigating liquid is transferred away from the expandable retention element, either directly to the catheter tip for flushing of the user's bowel without the irrigating liquid passing into or through the reservoir, or back to the reservoir.

The control system may be configured to control a flow condition of the irrigating liquid at the catheter tip during anal or stoma irrigation. The control system may hence comprise a controller for controlling operation of the pump, at least one sensor for determining a measure of pressure at at least one first predetermined position in the tubing system and/or the catheter during operation of the pump, and a processor for determining or estimating said flow condition at the catheter tip on the basis of said measure of pressure. Further, the control system may be configured to control the pumping operation of the pump in response to said measure of pressure.

The provision of the at least one sensor for determining a measure of pressure at at least one first predetermined position in the tubing system and/or the catheter during operation of the pump allows the processor to determine or estimate a flow condition at the catheter tip on the basis of such measure. For example, the rise of the pressure at a particular flow restrictor within the tubing system to a predetermined level may indicate the presence of irrigating liquid at the tip of the catheter. Similarly, the rise of pressure at the catheter tip itself may indicate the presence of irrigating liquid at the tip.

In one embodiment, the control system may comprise a memory for storing at least one pressure threshold value indicative of the presence of the irrigating liquid at at least the first predetermined position in the tubing system and/or the catheter and/or at at least one second predetermined position in the tubing system and/or the catheter. In such an embodiment, the control system may be configured to continue the pumping operation of the pump for a limited period of time after determination, by the at least one sensor, of a pressure value at the at least one first predetermined position which is at least equal to the pressure threshold value or a value derived therefrom. For example, one of the first and second predetermined positions may be a position at the catheter tip or in the vicinity thereof, in which case the control system may be configured to continue said pumping operation for a certain duration after the determination of said pressure threshold value. Accordingly, the amount of irrigating liquid expelled from the catheter tip may be accurately controlled by control of said duration.

DETAILED DESCRIPTION OF THE DRAWING

Embodiments, and features of the various exemplary embodiments described in this application, may be combined with each other ("mixed and matched"), unless specifically noted otherwise.

Figure 1:
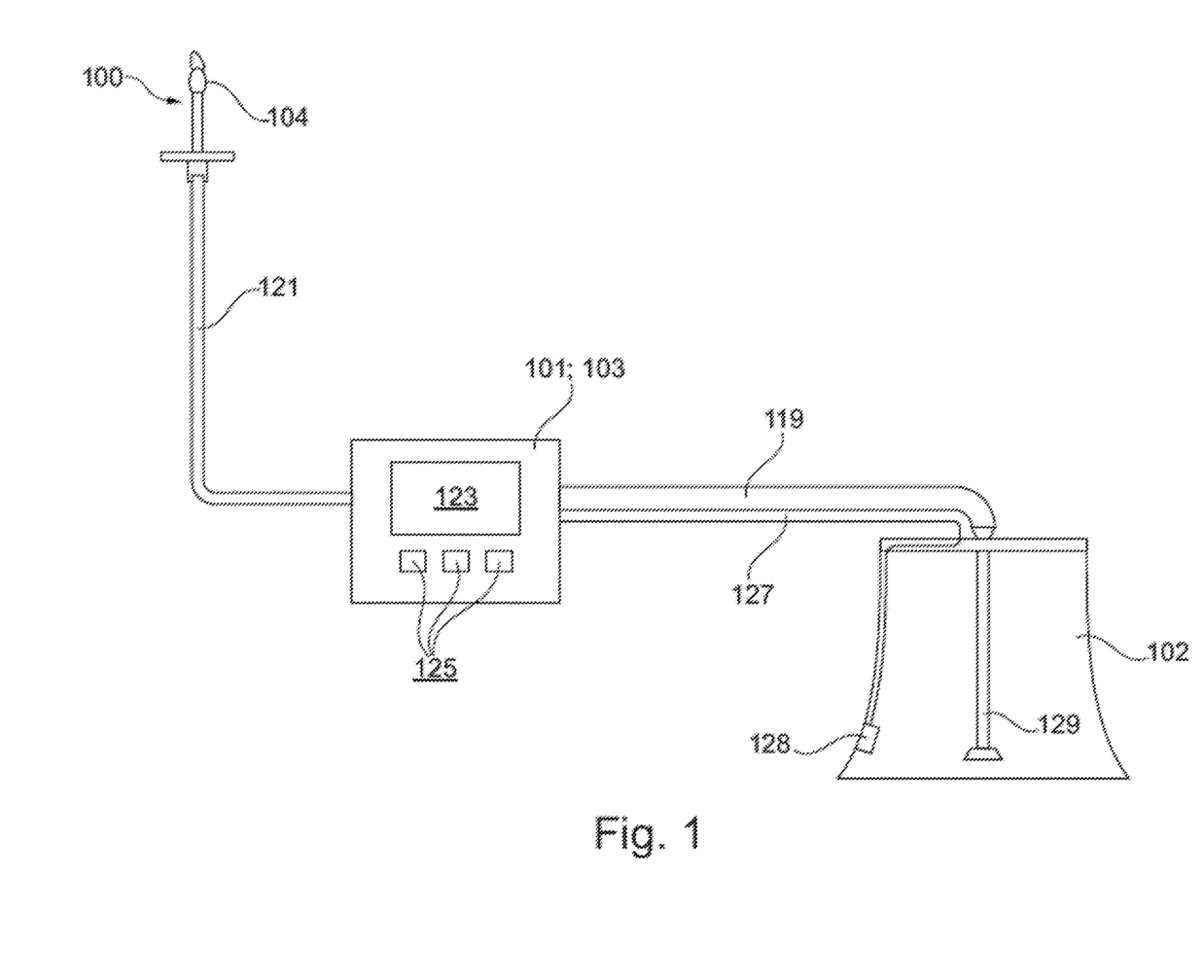
FIG. 1 shows an embodiment of a system for anal and/or stomal irrigation.

FIG. 1 shows an embodiment of a system for anal and/or stomal irrigation. The system comprises a catheter 100 sized and configured for insertion into the rectum or stoma of a user. A housing for a pump 101 is provided for transferring an irrigating liquid contained within a reservoir 102 to the catheter 100 and to an expandable retention element 104 in the form of a balloon configured to fixate the catheter within the user's rectum or stoma. A control system 103 for the pump and a valve system (not visible in FIG. 1) is further housed within the housing of the pump 101. Tube portion 119 connects the reservoir 102 to the pump 101, and tube portion 121 connects the pump within the housing of the pump 101 to the catheter 100 and expandable retention element 104. As discussed in further detail in relation to FIGS. 2-5 below, tube portion 121 includes separate conduits for connecting the pump to the catheter for expelling of irrigating liquid from the catheter tip and for expansion of the balloon 104, respectively. Tube portion 119 attaches to dip tube 129 for sucking irrigating liquid from the reservoir 102. The housing of the pump 101 is provided with a display 123 for communicating an operating state of the system and/or an asymptotic temperature value to the user, and user-operable control buttons 125 are provided as part of a user operable control interface for controlling operation of the valve system (not visible in FIG. 1) and/or pump 101. A thermo sensor 128 attaches to a wall of the reservoir 102, a wired connection 127 being provided for communicating a signal from the thermo sensor 128 to the control system 103 within housing of the pump 101.

Figure 2:
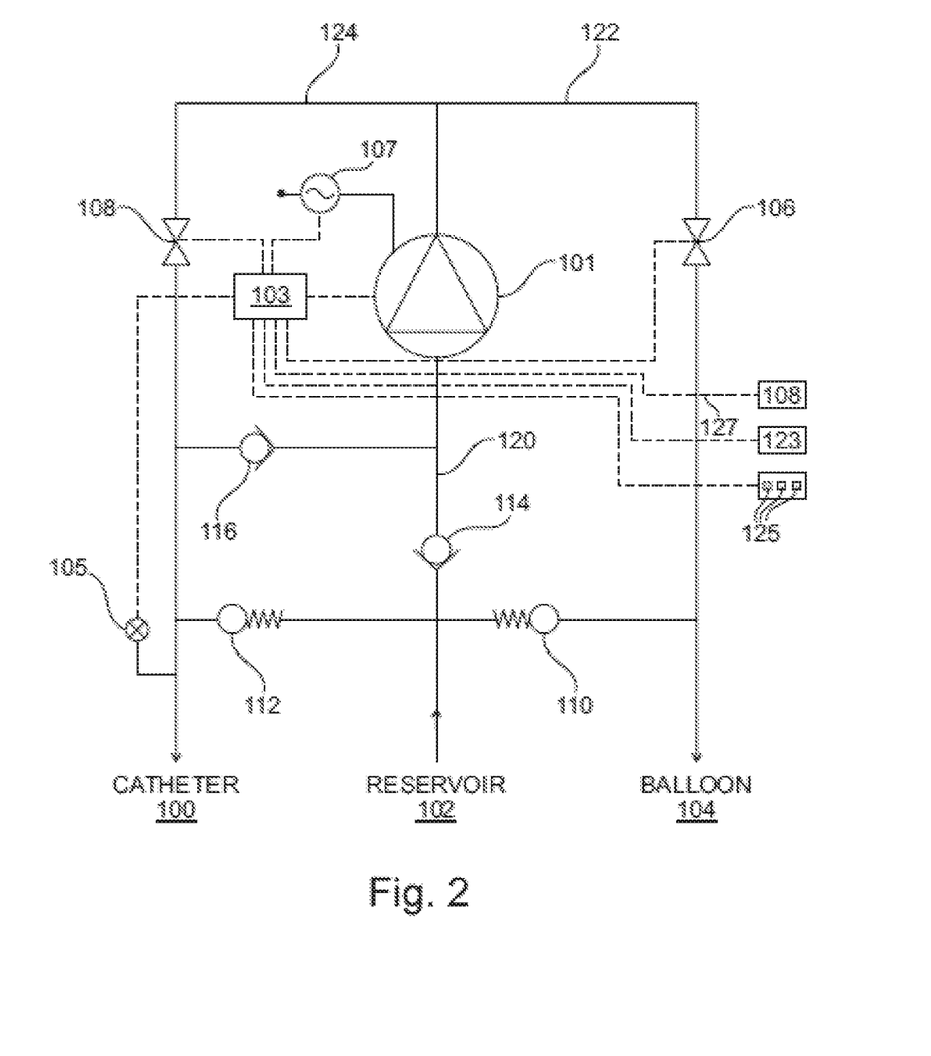
FIG. 2 shows an embodiment of a tubing and valve system of an embodiment of a system for anal and/or stomal irrigation.

FIG. 2 illustrates an embodiment of a tubing and valve system of the system of FIG. 1. As shown, pump 101 is connected to reservoir 102 via conduit 120 comprising a first check valve 124. The conduit 120 is provided within tube portion 119 (see FIG. 1). The first check valve 114 may be provided within tube portion 119, or within the housing of the pump 101, or within the dip tube 129. Downstream of the pump (when seen in flow direction from the reservoir towards the catheter 100 and the balloon 104), the tubing system has two branches, one of which includes conduit 122 connecting to the balloon 104 via a first actively controllable valve 106. The conduit 122 is provided within tube portion 121. The first actively operable valve 106 may be provided within the tube portion 121, or within the catheter 100, or within the housing of the pump 101. The other branch of the tubing system downstream of the pump includes conduit 124 connecting to the catheter 100 via a second actively controllable valve 108. The conduit 124 is provided within tube portion 121. The second actively operable valve 108 may be provided within the tube portion 121, or within the catheter 100, or within the housing of the pump 101. As shown by dashed lines in FIGS. 2-5, the actively controllable valves 106 and 108 are controllable by the control system 103.

A pressure sensor 105 is provided for measuring pressure at at least one first predetermined position in the tubing system 119, 120, 121, 122, 124 and/or the catheter 100 during operation of the pump 101. The pressure sensor 105 outputs a signal to the control system 103, which operates the pump and/or the actively controllable valves 106, 108 on the basis of said signal and other signals as described herein. The control system 103 includes a processor for determining or estimating a flow condition at the catheter tip on the basis of the measure of pressure provided by pressure sensor 105, and the control system is configured to control the pumping operation of the pump in response to said measure of pressure. More specifically, the control system continues pumping operation of the pump 101 for a limited period of time after determination, by the pressure sensor 105, of a pressure value which is at least equal to a pressure threshold value or a value derived therefrom. Thus, the amount of irrigating liquid expelled from the catheter tip may be accurately controlled. In the embodiment shown, the pressure sensor 105 is arranged in the tubing system 121, 124 in the vicinity of the catheter 100 or within the catheter 100 itself.

Control system 103 further receives input from user-operable control buttons 125, and thermo sensor 128, and control system 103 communicates data to display 123. The data communicated to display 123 may include a predicted future asymptotic value of the temperature of the irrigating liquid within the reservoir 102 as determined by thermo sensor 128. The data may be continuously updated as the control system 103 continuously updates the temperature prediction while irrigating liquid is being filled or re-filled into the reservoir.

First and second relief valves 110 and 112 are provided for allowing irrigating liquid to escape from the balloon 104 or from the catheter 100 in case the pressure therein exceeds the threshold pressure defined by the relief valves. The first relief valve 110 drains liquid from the balloon 104 to the reservoir 102 in the case of excessive pressure within the balloon 104, and the second relief valve drains liquid from the catheter 100 to the reservoir 102 in the case of excessive pressure within the user's rectum or stoma.

Further, first and second check valves 114 and 116 are provided for preventing undesired backflow of liquid in the tubing system. The first check valve 114 is provided within conduit 120 between the pump 101 and the reservoir 102 in order to prevent backflow of irrigating liquid from the pump 101, or any position downstream of the pump, to the reservoir 102. The second check valve 116 is provided in a side branch in the tubing system connecting conduit 124 to conduit 120. The first and second check valves 114 and 116 may be provided within tube portions 119 and 121 (see FIG. 1) or within the housing of the pump 101, or alternatively the first check valve 114 may be provided in dip tube 129. Second check valve 116 may be provided within the catheter 100.

Figure 3:
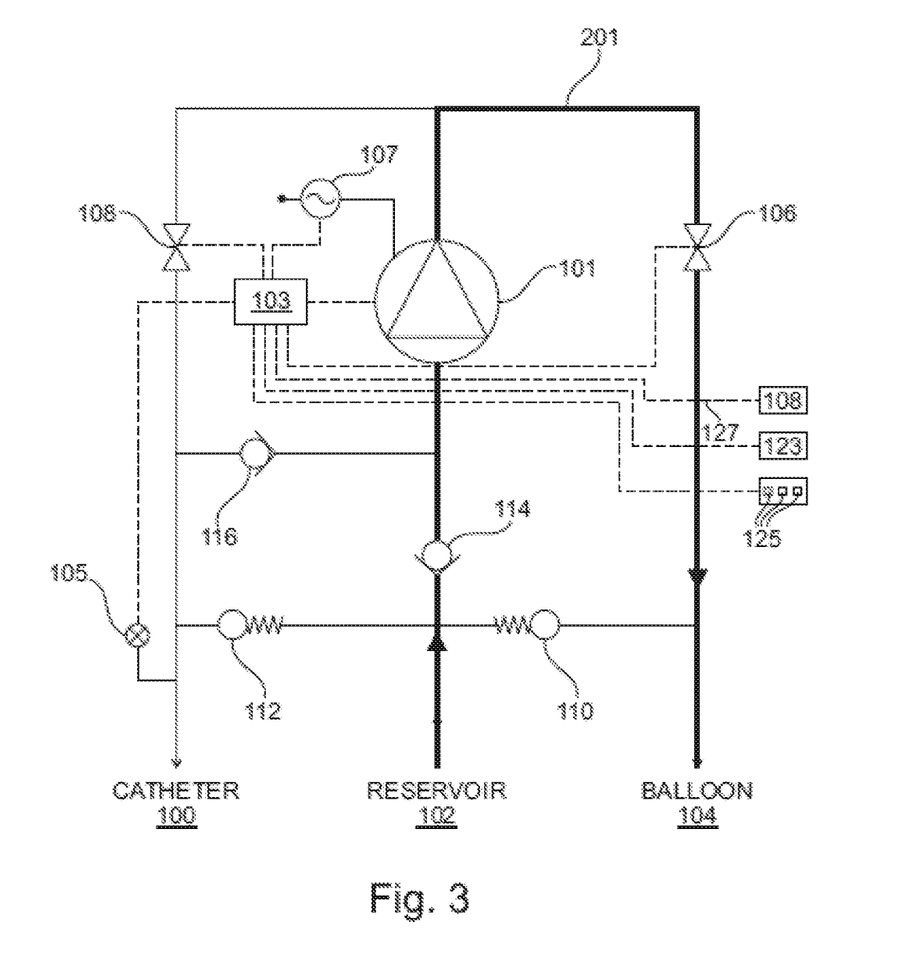
FIGS. 3-5 show respective embodiments of flow configurations in the tubing and valve system of FIG. 2.
Figure 4:
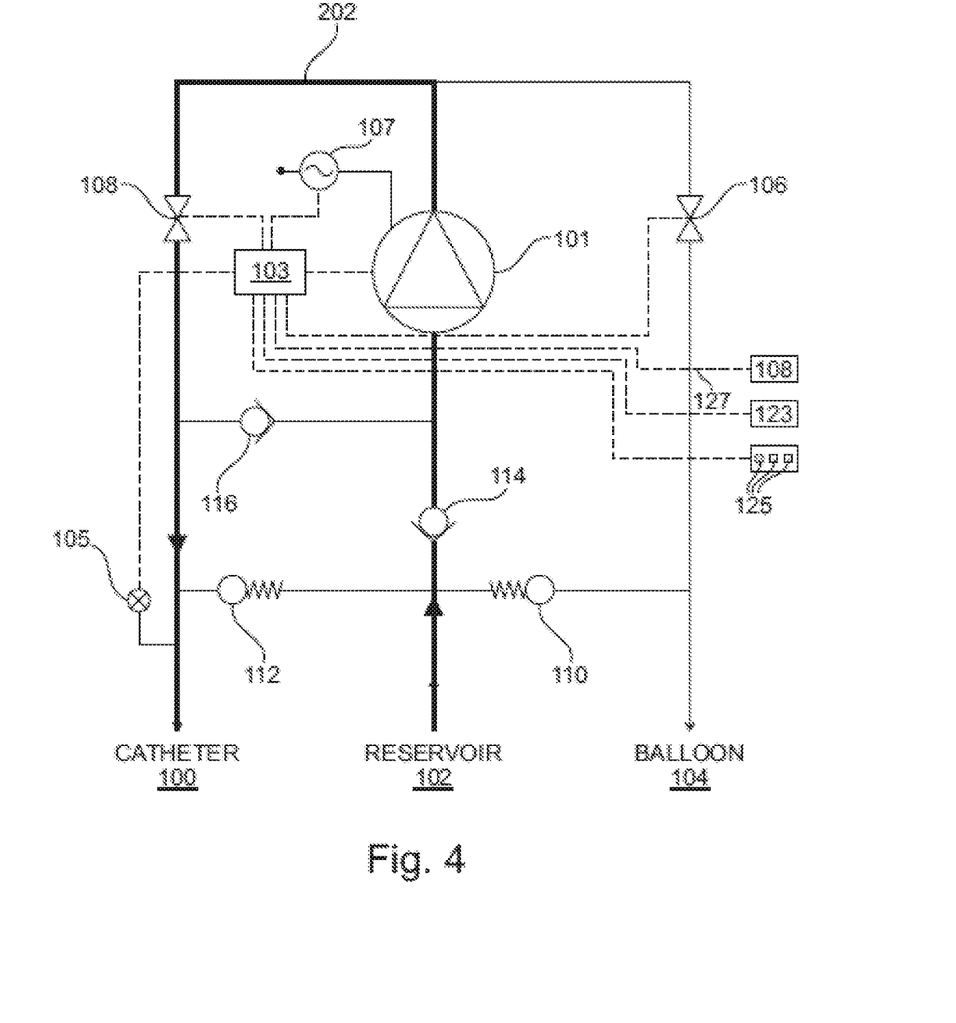
Figure 5:
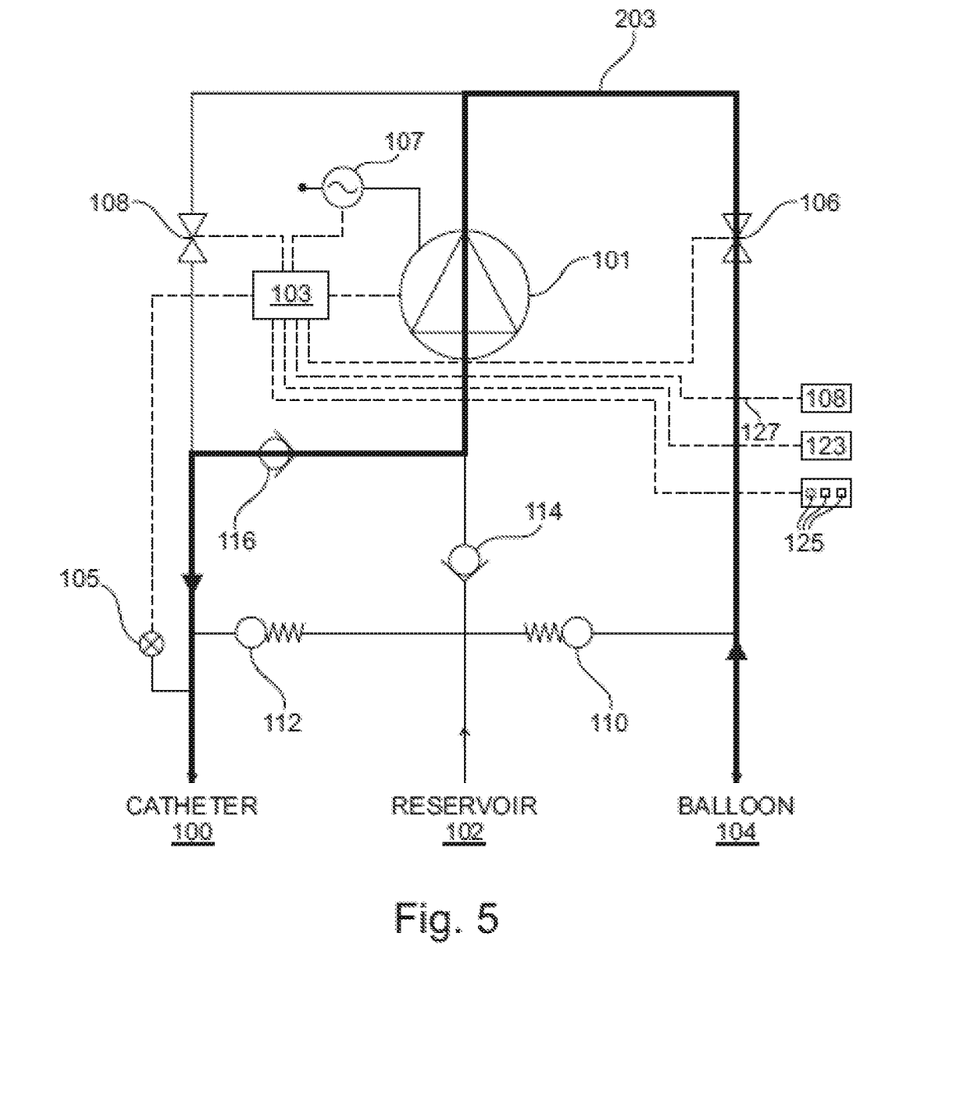

FIGS. 3-5 show respective embodiments of flow configurations in the tubing and valve system of FIG. 2. In the first flow configuration 201 shown in FIG. 3, the first actively controllable valve 106 is open, and the second actively controllable valve 108 is closed while the pump 101 operates. Accordingly, irrigating liquid is transferred from the reservoir 102 to the balloon 104 for expansion thereof. In the second flow configuration 202 shown in FIG. 4, the second actively controllable valve 108 is open, and the first actively controllable valve 106 is closed while the pump 101 operates. Irrigating liquid is thus transferred from the reservoir 102 to the catheter 100, at the tip of which the liquid is expelled into the user's rectum or stoma so as to irrigate the user's bowel. In the third flow configuration 203 shown in FIG. 5, operation of the pump 101 is reversed, and the first actively controllable valve 106 is open, while the second actively controllable valve 108 is closed. The balloon 104 is hence purged, and the irrigating liquid withdrawn therefrom flows from the balloon 104 to the catheter 100, at the tip of which it is expelled.

Figure 6:
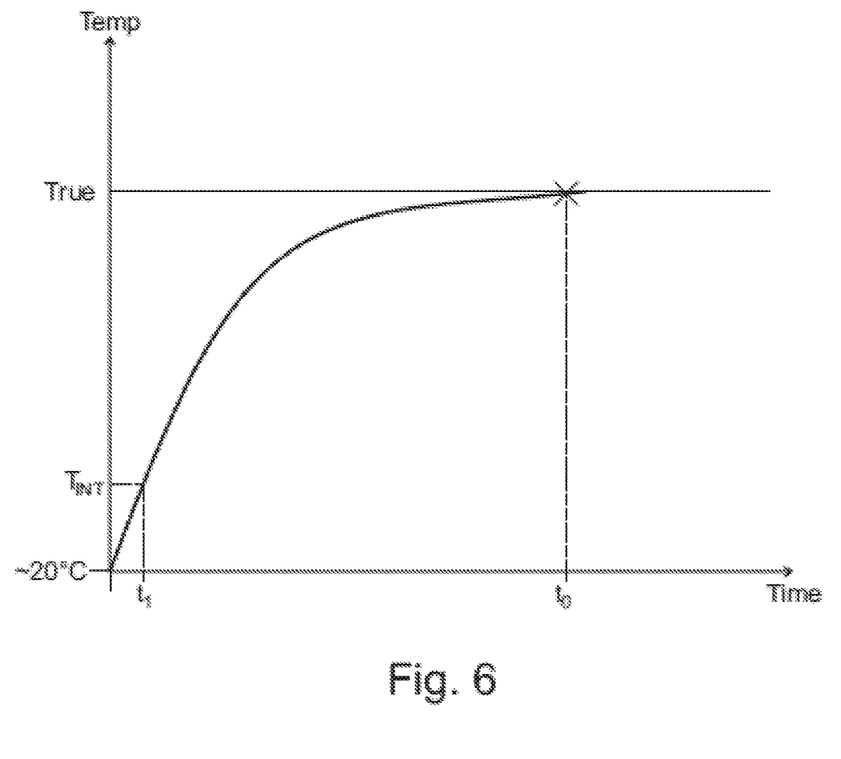
FIGS. 6 and 7 illustrate exemplary curves of temperature of an irrigating liquid in a reservoir during filling or refilling of irrigating liquid into the reservoir.
Figure 7:
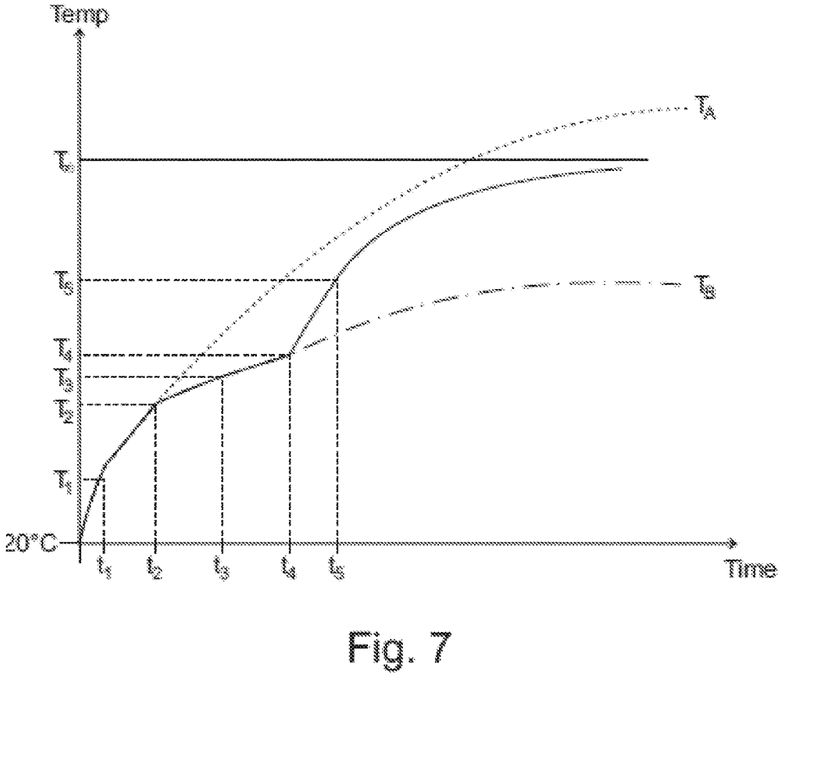

FIGS. 6 and 7 illustrates exemplary curves of temperature of the irrigating liquid in the reservoir 102 during filling or refilling of irrigating liquid into the reservoir. In the chart of FIG. 6, the initial temperature of the irrigating liquid within the reservoir 102 as determined by thermo sensor 128 is approximately 20° C. As the user's bowel should be irrigated with liquid at a temperature not exceeding approximately 40° C., preferably at a temperature of 20-40° C., most preferably at a temperature of 36-38° C., the user starts pouring liquid, such as tap water, at an elevated temperature into the reservoir.

Next, an initial change of the temperature within the reservoir is determined by the thermo sensor 128 upon commencement of filling or refilling of the irrigating liquid into the reservoir 120. In FIG. 6, the initial temperature change is represented by elevated temperature TINT at time t1. On the basis of the initial temperature change, a future asymptotic value of the temperature, denoted "True" in FIG. 6, within the reservoir is predicted on the basis of at least the initial change.

As shown in FIG. 7, a current temperature or a current rate of change of the temperature within the reservoir is continuously determined by means of thermo sensor 128 and control system 103, while the irrigating liquid is filled or refilled into the reservoir, and the prediction of the future asymptotic value of the temperature within the reservoir is continuously updated on the basis of at least said current temperature and/or rate of change of the temperature. More specifically, at the start of the filling or refiling procedure, an initial temperature change T1 is determined at a first point in time, t1. The first initial temperature change as represented by T1 is used for a first prediction, TA, of a future asymptotic temperature value of the irrigating liquid within the reservoir 102 once filled. At a second point in time, t2, when the temperature as determined by the thermo sensor 128 has reached level T2, the temperature of the liquid supplied to the reservoir changes, for example as the user changes the ratio of hot to cold water in the tap. At a third point in time t3, a third temperature value T3 is obtained, and second prediction TB is made. Subsequently, at a fourth point in time, t4, a fourth temperature level T4 is reached, and the temperature of the liquid filled into the reservoir 102 changes abruptly for a second time. The change of the supplied liquid is reflected by temperature T5 at time t5, on the basis of which a third asymptotic temperature prediction T∞ is made.

During the above procedure, the predicted temperature values TA, TB and T∞ are shown to the user via display 123 (see FIGS. 1-5) as they are determined by the control system 103.

Figure 8:
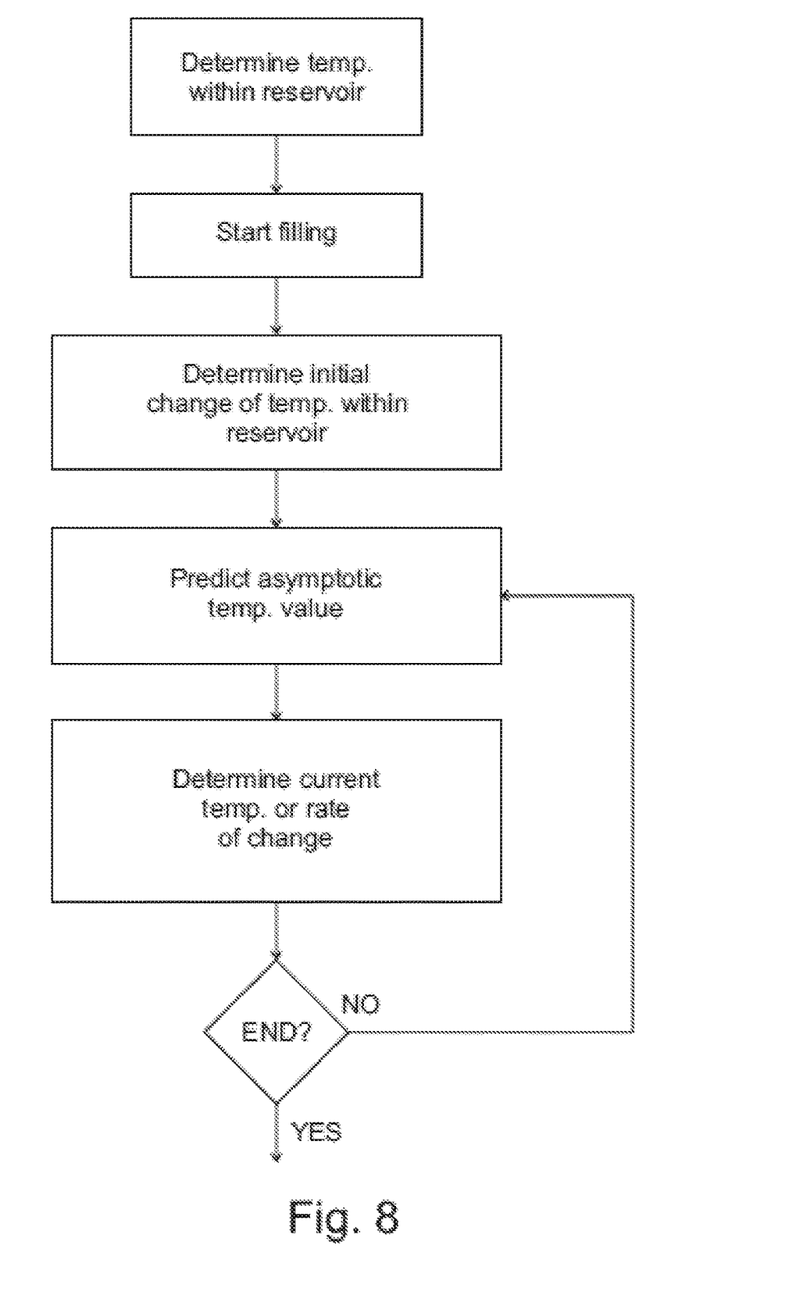
FIG. 8 illustrates an embodiment of a method for predicting a temperature of an irrigating liquid in a reservoir of a system for anal irrigation.

The above procedure of continuously determining and updating the asymptotic temperature prediction is generally depicted in FIG. 8.

Figure 9A:
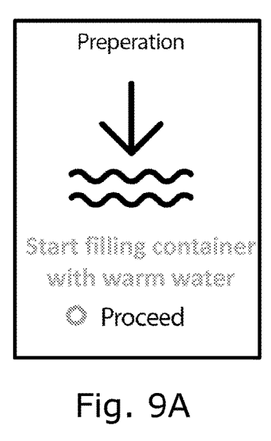
FIGS. 9A-9E illustrate a graphical user interface of an embodiment of a system and method.
Figure 9B:
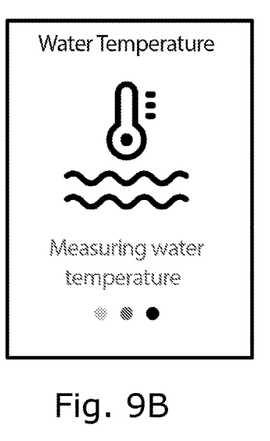
Figure 9C:
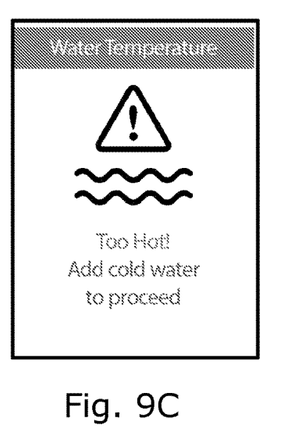
Figure 9D:
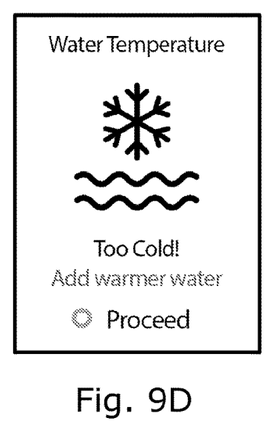
Figure 9E:
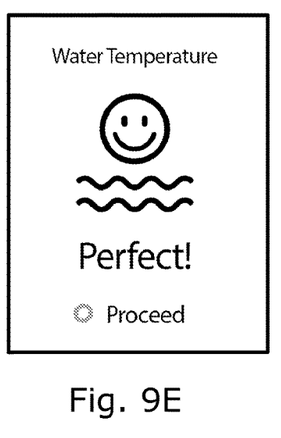

FIGS. 9A-9E illustrate an embodiment of a graphical user interface of a system and method. More specifically, FIG. 9 shows a display of such a user interface, in which an indication is provided to start filling the reservoir, i.e. container, with irrigating liquid, in this case warm water (FIG. 9A). In the illustration of FIG. 9B, the display has switched its display to indicate to the user that the water temperature is being determined. FIGS. 9C and 9D illustrate an optical warning signal in the display in case the current or predicted future temperature of the irrigating liquid is too high and too low, respectively. FIG. 9E shows an exemplary display in case of a current or predicted future temperature of the irrigating liquid which is within the desired interval of e.g. 36° C. and 38° C.

The invention claimed is:

1. A system for anal or stomal irrigation, the system comprising:
   a reservoir adapted to contain an irrigating volume of liquid;
   a catheter comprising a catheter tip;
   a tubing system providing a conduit for the irrigating volume of liquid between the reservoir and the catheter tip;
   a pump operable to pump the irrigating volume of liquid from the reservoir to the catheter tip;
   a thermo-sensor connected to the reservoir and configured to measure a temperature within the reservoir; and a control system operatively connected with the thermo-sensor, the control system configured to:

determine a first temperature within the reservoir before the irrigating volume of liquid is filled into the reservoir;

determine an initial change from the first temperature within the reservoir after adding a first portion of the irrigating volume of liquid having a second temperature into the reservoir;

continuously determine one of a current temperature and a rate of change of the current temperature of liquid in the reservoir; and continuously calculate an asymptotic temperature for the irrigating volume of liquid within the reservoir based on one of the current temperature and the rate of change of the current temperature, where the asymptotic temperature is in a range from 36-38 degrees Celsius; and display instructions to a user to add a second portion of the irrigating volume of liquid at a third temperature until the asymptotic temperature of the irrigating volume of liquid is obtained in the reservoir, where the third temperature is one of less than the second temperature and greater than the second temperature.

2. The system of claim 1, wherein the control system is configured to emit a warning signal if the current temperature or the asymptotic temperature is below a predetermined lower limit or above a predetermined upper limit.

3. The system of claim 1, wherein the thermo-sensor is arranged within an inner wall of the reservoir.

4. The system of claim 1, wherein the control system is configured to predict the asymptotic temperature within the reservoir based on the initial change and based on a thermal characteristic of the system.

5. The system of claim 4, wherein the thermo-sensor comprises a temperature sensitive element and a thermal conductor in contact with the temperature sensitive element, and the thermal characteristic of the system comprises a thermal characteristic of the thermal conductor.

6. The system of claim 5, wherein the temperature sensitive element is biased toward the thermal conductor.

7. The system of claim 4, wherein the thermo-sensor is mounted to a wall of the reservoir and the thermal characteristic of the system comprises a thermal characteristic of the wall of the reservoir.

8. The system of claim 1, wherein the system further comprises a display screen, and the control system is operatively connected to the display screen and configured to display the instructions to the user.

9. The system of claim 1, comprising configuring the control system to display instructions to a user to add warm tap water to the reservoir.

10. A method for predicting a temperature during anal or stomal irrigation, the method comprising:

providing an irrigation system having a reservoir adapted to contain an irrigating volume of liquid, a catheter comprising a catheter tip, a tubing system providing a conduit for the irrigating volume of liquid between the reservoir and the catheter tip, a pump operable to pump the irrigating volume of liquid from the reservoir to the catheter tip, a thermo-sensor connected to the reservoir, and a control system operatively connected with the thermo-sensor;

determining a first temperature within the reservoir before liquid is introduced into the reservoir;

adding a first portion of the irrigating volume of liquid having a first temperature into the reservoir and determining an initial change of temperature in the reservoir;

predicting a temperature of the irrigating volume of liquid in the reservoir based on the initial change of temperature within the reservoir; and instructing a user to add a second portion of the irrigating volume of liquid into the reservoir at a second temperature based on the predicted temperature of the irrigating volume of liquid in the reservoir, where the second temperature is one of less than the first temperature and greater than the first temperature, until the predicted temperature of the irrigating volume of liquid in the reservoir approaches an asymptotic temperature in a range from 36-40 degrees Celsius.

11. The method of claim 10, further comprising:

operating the control system to emit a warning signal if a measured temperature of liquid in the reservoir is below a predetermined lower limit or above a predetermined upper limit.

12. The method of claim 10, comprising instructing the user to add hot tap water into the reservoir until the predicted temperature of the irrigating volume of liquid in the reservoir approaches the asymptotic temperature in the range from 36-40 degrees Celsius.

13. The method of claim 10, comprising instructing the user to add cold tap water into the reservoir until the predicted temperature of the irrigating volume of liquid in the reservoir approaches the asymptotic temperature in the range from 36-40 degrees Celsius.

* * * * *